(12) United States Patent
Katagiri et al.

(10) Patent No.: US 8,207,501 B2
(45) Date of Patent: Jun. 26, 2012

(54) APPARATUS AND METHOD FOR MEASURING TERAHERTZ WAVE

(75) Inventors: Takashi Katagiri, Sendai (JP); Takeaki Itsuji, Hiratsuka (JP)

(73) Assignee: Canon Kabushiki Kaisha, Tokyo (JP)

( * ) Notice: Subject to any disclaimer, the term of this patent is extended or adjusted under 35 U.S.C. 154(b) by 194 days.

(21) Appl. No.: 12/742,905

(22) PCT Filed: Jan. 16, 2009

(86) PCT No.: PCT/JP2009/051019
§ 371 (c)(1),
(2), (4) Date: May 13, 2010

(87) PCT Pub. No.: WO2009/091078
PCT Pub. Date: Jul. 23, 2009

(65) Prior Publication Data
US 2010/0288928 A1     Nov. 18, 2010

(30) Foreign Application Priority Data

Jan. 18, 2008   (JP) .................................. 2008-009896
Nov. 26, 2008   (JP) .................................. 2008-300302

(51) Int. Cl.
G01J 5/02     (2006.01)
(52) U.S. Cl. .................................................. 250/341.1
(58) Field of Classification Search ............... 250/338.1, 250/338.4, 339.06, 341.1, 341.8
See application file for complete search history.

(56) References Cited

U.S. PATENT DOCUMENTS

| | | |
|---|---|---|
| 5,710,430 A | 1/1998 | Nuss |
| 7,248,995 B2 | 7/2007 | Itsuji et al. |
| 7,560,695 B2 | 7/2009 | Kasai et al. |
| 7,633,299 B2 | 12/2009 | Itsuji |
| 7,745,791 B2 | 6/2010 | Kasai et al. |
| 2007/0030115 A1 | 2/2007 | Itsuji et al. |
| 2008/0315098 A1 | 12/2008 | Itsuji |
| 2009/0146084 A1 | 6/2009 | Itsuji |
| 2009/0189078 A1 | 7/2009 | Itsuji |
| 2009/0213880 A1 | 8/2009 | Ouchi et al. |

FOREIGN PATENT DOCUMENTS

JP     3387721 B2     3/2003

OTHER PUBLICATIONS

Itsuji, Takeaki, et al., "Waveform Information Acquisition Apparatus and Waveform Information Acquisition Method", U.S. Appl. No. 12/680,889, filed Mar. 30, 2010.
Kasai, Shintaro, et al., "Inspection Apparatus and Inspection Method Using Electromagnetic Wave", U.S. Appl. No. 12/682,248, filed Apr. 8, 2010.
International Preliminary Report on Patentability dated Jul. 29, 2010 in corresponding PCT Patent Application No. PCT/JP2009/051147.
Ferguson et al., "Identification of biological tissue using chirped probe THz imaging", Microelectronics Journal 33, (2002), pp. 1043-1051.
Nuss, "Chemistry is Right for T-Ray Imaging", IEEE Circuits and Devices Magazine, vol. 12, No. 2 (1996), pp. 25-30.

*Primary Examiner* — Mark R Gaworecki
(74) *Attorney, Agent, or Firm* — Fitzpatrick, Cella, Harper & Scinto

(57) ABSTRACT

An apparatus for measuring a terahertz wave includes a dispersing section 103 for chirping the terahertz wave 104 generated from a generating section 101. A detecting section 102 detects waveform information on the terahertz wave chirped by the dispersing section 103. As a result, it is possible to acquire frequency information included in the waveform information. Therefore, it is possible to acquire spectral information including amplitude information of each frequency component and intensity information on each frequency or wavelength from the time waveform without Fourier-transforming the time waveform.

8 Claims, 9 Drawing Sheets

APPARATUS AND METHOD FOR MEASURING TERAHERTZ WAVE

TECHNICAL FIELD

This invention relates to an apparatus for measuring a terahertz wave and a measuring technique for acquiring information on an object of examination. More particularly, this invention relates to a measuring apparatus and a measuring method for acquiring information on physical properties of an object of examination by means of an electromagnetic wave which is typically a terahertz wave (an electromagnetic wave having a frequency band not less than 0.3 THz and not more than 30 THz for this specification).

BACKGROUND ART

A terahertz wave has major characteristics as listed below.

Firstly, since the wavelength of a terahertz wave is relatively short, it is transmitted through a non-metal substance just like X-rays. Secondly, there are many biomolecules and medicines having a characteristic absorption spectrum in the frequency band of terahertz wave. Thirdly, it has spatial resolving power suited for various imaging applications because the pulse width in time domain is relatively short.

Fields of application of terahertz waves having characteristics as listed above include spectral analysis techniques for the inside of substance, safe see-through imaging apparatus that can replace X-ray fluoroscopic apparatus and techniques for analyzing biomolecules.

Japanese Patent No. 3387721 discloses that THz-TDS (terahertz time domain spectroscopy) can suitably be used as spectroscopy for employing a terahertz wave. FIG. 10 of the accompanying drawings schematically illustrates an apparatus realized by applying terahertz time-domain spectroscopy.

Referring to FIG. 10, femtosecond light pulse L1 emitted from a femtosecond pulse light source 901 that is a titanium-sapphire laser is split to produce two light pulses L2 and L3 by a beam splitter 902. The light pulse L2 excites terahertz pulse generator 903 to generate a terahertz pulse T1. On the other hand, the light pulse L3 is optically delayed by a light pulse delaying section 907 that is formed by using a combination of several planar reflectors and a moving mirror. The optically delayed light pulse L4 is made to enter a terahertz pulse detector 906 by way of a mirror 908.

A photoconductive antenna formed by depositing a dipole antenna on an LT-GaAs thin film that is grown on a GaAs substrate at low temperatures can suitably be employed for both the terahertz pulse generator 903 and the terahertz pulse detector 906. Excited carriers are accelerated to generate a terahertz pulse T1 in the generator 903 as a femtosecond laser pulse L2 is driven to strike the gap of the dipole antenna as pump light in a state where a voltage is applied to the gap. On the other hand, as a femtosecond laser pulse L4 is driven to strike the gap as probe light in the detector 906, an electric current signal that is proportional to the electric field of the terahertz pulse at the time when probe light strikes the gap is generated.

The terahertz pulse T1 generated by the terahertz pulse generator 903 is focused by a focusing optical system 904. An object of examination 100 is arranged at the focus position. The terahertz pulse T2 transmitted through the object of examination 100 is made to enter the terahertz pulse detector 906 by the focusing optical system 905. As pointed out above, an electric current signal that is proportional to the electric field of the terahertz pulse T2 at the time when probe light L4 strikes the gap is generated in the terahertz pulse detector 906. This signal is amplified by an amplifier 909 and then taken into adjusting section 910 that is formed by a signal processing circuit, a personal computer and so on.

The time waveform of the terahertz pulse T2 can be acquired by sequentially changing the optical delay by means of the light pulse delaying section 907 and observing the terahertz pulse, changing the timing of detection. Spectral information (amplitude information on each frequency component, intensity information on each frequency (wavelength) etc. can be obtained by Fourier-transforming the time waveform.

A two-dimensional image of the object of examination 100 can be obtained by scanning the object of examination 100 on a plane perpendicular to the optical axis by means of a scanning stage 912. Then, a so-called spectral image that provides spectral information on each pixel of the two-dimensional image can be obtained by observing the time waveform of the terahertz pulse on a pixel by pixel basis by using the same technique. Such an image can be displayed on a display section 911.

DISCLOSURE OF THE INVENTION

The object of the present invention is to provide an apparatus for measuring a terahertz wave that can acquire spectral information from a time waveform without Fourier-transforming the time waveform.

An apparatus for measuring a terahertz wave according to the present invention includes a generating section for generating a terahertz wave, a dispersing section for chirping a terahertz wave generated from the generating section, and a detecting section for detecting waveform information on a terahertz wave chirped by the dispersing section, the apparatus acquiring frequency information from the waveform information.

In another aspect of the present invention, there is provided a method of measuring a terahertz wave including generating a terahertz wave, chirping the generated terahertz wave, detecting waveform information on the chirped terahertz wave, and acquiring frequency information from the waveform information.

In still another aspect of the present invention, there is provided a method of measuring a terahertz wave including generating a first terahertz wave, chirping the generated first terahertz wave, detecting waveform information on the chirped first terahertz wave, generating a second terahertz wave, chirping the generated second terahertz wave, detecting waveform information on the chirped second terahertz wave, acquiring a time waveform of a terahertz wave from the waveform information on the first and second terahertz waves by differentiating a timing of generating or detecting the second terahertz wave from a timing of generating or detecting the first terahertz wave, and obtaining frequency information by using the time waveform.

In view of the above-identified problem, according to the present invention, there is provided a terahertz pulse measuring apparatus for acquiring information on an object of examination, including an irradiation section, a detecting section, a dispersing section and an adjusting section. The irradiation section irradiates a terahertz pulse to the object of examination. The detecting section detects the electric field intensity of the terahertz pulse transmitted through or reflected by the object of examination. The dispersing section is arranged on the optical path of the terahertz pulse and has a function of frequency-chirping the terahertz pulse. The adjusting section adjusts the timing of detection for detecting the electric field intensity of the frequency-chirped terahertz pulse in the detecting section.

In view of the above-identified problem, according to the present invention, there is provided a terahertz pulse measuring method of acquiring information on an object of examination, including an irradiation step, a dispersion step, a detection step and an adjustment step. A terahertz pulse is irradiated to the object of examination in the irradiation step. The terahertz pulse is frequency-chirped on its optical path in the dispersion step. The electric field intensity of the frequency-chirped terahertz pulse that is transmitted through or reflected by the object of examination is detected at a timing of detection that corresponds at least to a frequency to be measured in the detection step. The timing of detection for detecting the electric field intensity is adjusted in the adjustment step.

In this way, the terahertz wave is chirped and the time waveform is made to include information on frequencies by using a dispersing section. Then, as a result, spectral information can be obtained from the time waveform without Fourier-transforming the time waveform.

Further features of the present invention will become apparent from the following description of exemplary embodiments with reference to the attached drawings.

BEST MODE FOR CARRYING OUT THE INVENTION

Now, an embodiment of apparatus for measuring a terahertz wave according to the present invention will be described below by referring to FIG. 1A.

Figure 1A:
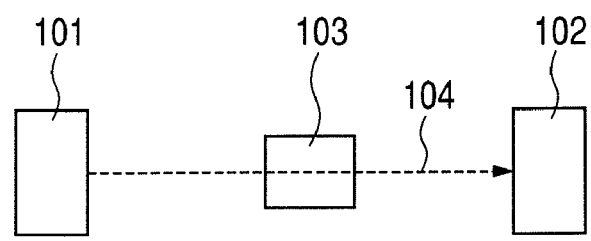
FIGS. 1A, 1B and 1C are schematic illustrations of an embodiment of apparatus for measuring a terahertz wave according to the present invention.

In FIG. 1A, 101 is a generating section for generating a terahertz wave. The generating section 101 can be a photoconductive semiconductor (a structure having a single layer, to be also referred to as photoconductive film hereinafter) of GaAs (LT-GaAs), InGaAs or AlGaAs grown at low temperatures. The generating section 101 can also be a structure formed to include a photoconductive semiconductor (having a plurality of layers). More specifically, the structure is a diode structure (a structure having a current rectifying property) formed to include a semiconductor having an energy band gap smaller than photon energy of excitation light. Examples of diode structure that can be used for the purpose of the present invention include a p-i-n diode structure, a metal-i-n diode structure, a metal-i-metal diode structure and a Schottky barrier diode structure. Such structures can reduce the electric current made to flow by carriers generated by irradiation of excitation light by applying an inverse bias to the element. Therefore, it is possible to efficiently apply an electric field to carriers if the generating section 101 shows a low resistance. A material showing a resistance lower than the resistance of LT-GaAs such as InGaAs can be used for the i layer but the present invention is by no means limited to the user of such a material. A resonant tunneling diode, a semiconductor superlattice or a superconductor may alternatively be used for the generating section 101.

In FIG. 1A, 102 is a detecting section for detecting waveform information on the terahertz wave. A structure similar to that of the generating section 101 may be adopted for the detecting section 102.

Waveform information of a terahertz wave (the waveform information detected by the detecting section 102) to be used for the purpose of the present invention will be described below. Firstly, the waveform information may be intensity information (electric field intensity, amplitude value) to be acquired by changing the timing of detection for each generated terahertz wave. If such is the case, the time waveform (the waveform of the terahertz wave using the time axis as horizontal axis) can be reconfigured from a plurality of pieces of such intensity information.

Secondly, waveform information of a terahertz wave may be the waveform information detected by following the terahertz wave on a real time basis or information relating to the envelope of the time waveform. If such is the case, it is desirable that the width of the waveform of the terahertz wave is large (stretched) on the time axis thereof so that the terahertz wave can be followed and detected on a real time basis.

It is not necessary to acquire all the time waveform. For example, it may be sufficient to adjust the timing of detection so as to acquire the electric field intensity relating to a desired frequency by means of the adjusting section. The adjusting section will be described in greater detail hereinafter.

Figure 1B:
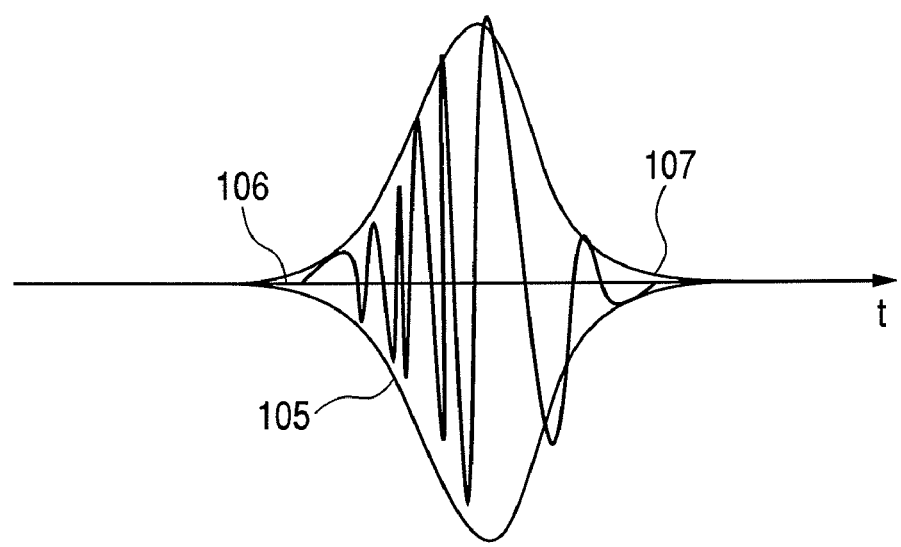

In FIG. 1A, 103 is a dispersing section for chirping the terahertz wave generated from the generating section 101. The characteristics and the structure of the dispersing section 103 will be described in greater detail hereinafter. For the purpose of the present invention, the term of "chirp" refers to arranging pieces of intensity information (electric field intensity, amplitude value) for respective frequencies (wavelengths) in the ascending order of the frequencies (wavelengths). Note that terahertz pulse 105 is arranged in the ascending order of wavelengths (from short wavelength 106 to long wavelength 107) relative to the time axis in FIG. 1B.

Thus, the dispersing section 103 can detect waveform information on the chirped terahertz wave as described above. Then, it is possible to acquire information on the frequencies included in such waveform information.

In FIG. 1A, 104 denotes a terahertz wave being propagated. The terahertz wave 104 is preferably pulse-shaped (a terahertz pulse).

Known apparatus for examining substances (and identifying the substances) by means of a terahertz wave rely on THz-TDS (terahertz time domain spectroscopy). Then, the apparatus acquires the time waveform of the terahertz wave and Fourier-transforms the time waveform to acquire information on frequencies (the electric field intensity or the amplitude value of each frequency).

This embodiment positively disperses a terahertz wave so as to make spectral information to be included in the time waveform. With such an arrangement, it is possible to acquire information on absorption of frequencies directly from the time waveform of the terahertz wave transmitted through or reflected by a substance. Then, it is possible to identify an object of examination from the change in the time waveform due to the presence or absence of the object of examination without any Fourier transform.

(Detection by Following Terahertz Wave on Real Time Basis)

The detecting section 102 is a detector that can follow the terahertz wave that is chirped by the dispersing section 103 on a real time basis (the detecting time is shorter than the width of the waveform of the terahertz wave on the time axis). A Schottky barrier diode, which will be described in greater detail hereinafter, is preferably employed for the detecting section 102.

The waveform information detected by the detecting section 102 is information on the waveform where the pulse intensities of frequencies are arranged in the order of the frequencies relative to time.

The dispersing section 103 preferably uses normal dispersion. Then, the frequency band of the terahertz wave can be broadened by SPM (self phase modulation) when the power (electric field intensity, amplitude value) of the terahertz wave is raised.

The time waveform of a terahertz pulse is acquired by means of THz-TDS according to the prior art because the terahertz pulse cannot be detected on a real time basis. This is because the pulse width is narrower (shorter) than the detection time (detection speed) on the time axis of the terahertz pulse.

(Acquisition of Information on Time Waveform by Means of Delaying Section)

Figure 1C:
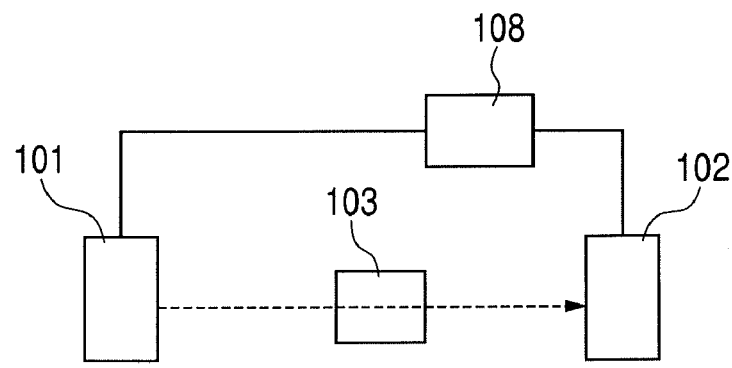

Another embodiment will be described below by referring to FIG. 1C.

An apparatus for measuring a terahertz wave according to the present invention preferably has a delaying section 108 for changing the timing of generating or detecting a terahertz wave.

The detecting section 102 detects intensity information on each terahertz wave generated from the generating section 101 and chirped by the dispersing section. At this time, the timing of generating or detecting the terahertz wave is differentiated.

Then, information on frequency is acquired by using information on the time waveform of the terahertz wave acquired from the detected plurality of pieces of intensity information.

Information on the time waveform is information on the waveform where pieces of intensity information for respective frequencies are arranged in the order of frequencies relative to time.

An apparatus for measuring a terahertz wave according to the present invention preferably has an adjusting section for adjusting the timing of generating a terahertz wave from the generating section 101 or the timing of detecting the terahertz wave by the detecting section 104 according to the information on frequencies. Such an adjusting section will be described in greater detail hereinafter.

The adjusting section preferably includes an extremum-finding section for finding an extremum of the electric field intensity near the timing of detection of detecting the intensity information by the detecting section relative to the time of information on the time waveform.

(Method)

Another embodiment of method of measuring a terahertz wave according to the present invention has at least the following steps:

1) a step of generating a terahertz wave;
2) a step of chirping the generated terahertz wave;
3) a step of detecting waveform information on the chirped terahertz wave; and
4) a step of acquiring frequency information from the waveform information.

When waveform information on terahertz wave is intensity information (electric field intensity, amplitude value) to be acquired by changing the timing of detection for each generated terahertz wave, the method has at least the following steps:

1) a step of generating a first terahertz wave;
2) a step of chirping the generated first terahertz wave;
3) a step of detecting waveform information on the chirped first terahertz wave;
4) a step of generating a second terahertz wave;
5) a step of chirping the generated second terahertz wave;
6) a step of detecting waveform information on the chirped second terahertz wave;
7) a step of acquiring information on a time waveform of a terahertz wave from the waveform information on the first and second terahertz waves by differentiating the timing of generating or detecting the second terahertz wave from the timing of generating or detecting the first terahertz wave; and
8) a step of obtaining frequency information by using the time waveform.

Information on an entire time waveform may be formed from waveform information. Alternatively, information on an entire time waveform may be formed from information on several spots on the time waveform. Still alternatively, no time waveform may be formed.

(Terahertz Pulse Measuring Apparatus and Terahertz Pulse Measuring Method)

Now, still other embodiments of the present invention will be described below.

With THz-TDS described above, it sometime takes tens of several seconds to several minutes to acquire the time waveform of a terahertz pulse by measurement. Therefore, spectral information cannot be acquired with ease by measurement when the measurement needs to be conducted at high speed or the object of examination moves as in the case of a living thing. Additionally, for acquiring two-dimensional or three-dimensional spectral information, at least a time length equal to the product of multiplication of the time for acquiring the time waveform and the number of pixels is required as shooting time.

To achieve such an effect, another embodiment of measuring apparatus and another embodiment of measuring method respectively have the basic components and the basic steps listed below. Namely, the measuring apparatus has a detecting section for detecting the electric field intensity of the terahertz pulse from the object examination irradiated with the terahertz pulse and a dispersing section arranged on the optical path of the terahertz pulse and having a function of frequency-chirping the terahertz pulse. Then, amplitude information on the terahertz pulse coming from the object of examination can be obtained for the frequency to be observed by adjusting the timing of detection of detecting the electric field intensity in the detecting section by the detecting section.

The measuring method has a dispersion step of frequency-chirping the terahertz pulse on the optical path thereof. Then, the timing of detection of detecting the electric field intensity can be adjusted so as to detect the electric field intensity of the frequency-chirped terahertz pulse coming from the object of examination irradiated with the terahertz pulse at a timing of detection that matches at least a frequency to be observed.

Thus, with the embodiments, it is possible to detect a frequency-chirped terahertz pulse at a timing that matches the frequency to be observed. Then, it is possible to acquire amplitude information for the frequency to be observed without acquiring the time waveform of the terahertz pulse. Therefore, information on physical properties of an object of examination can be obtained relatively at high speed. Additionally, a frequency to be observed can be selected flexibly from a broad frequency range.

Thus, with the above-described basic arrangement, it is possible to acquire information on physical properties of an object of examination relatively at high speed by acquiring amplitude information on the terahertz pulse coming from the object of examination for the frequency to be observed without acquiring the entire time waveform of the terahertz pulse. More specifically, information on the object of examination arranged between the irradiation section and the detecting section is acquired from the change in the state of propagation of the terahertz pulse from the object of examination for the frequency to be observed. It is sufficient for acquiring the amplitude information that the ratio of the pulse frequency of the electromagnetic wave generated by the irradiation section to the sampling frequency at which the propagated electromagnetic wave is taken into the detecting section is equal to n:1 (n=a natural number not smaller than 1). Typically, the pulse frequency agrees with the sampling frequency. Additionally, the time width of the terahertz pulse generated by the irradiation section is made sufficiently large relative to the time width of sampling and the terahertz pulse is generated substantially simultaneously with the timing of sampling for detection for these embodiments. While the above described effect is achieved by frequency-chirping the terahertz pulse in the optical path thereof by the dispersing section or in the dispersion step and adjusting the timing of detection of detecting the electric field intensity, various modes of realization can feasibly be used for the purpose of the present invention as described below within the above basic arrangement.

In the embodiment and the examples that are described hereinafter, a photoconductive switch element or an electro-optic crystal of a semiconductor such as gallium arsenide is employed and a terahertz pulse is generated by optical gating using pump light, while sampling is conducted by way of optical gating using probe light. However, it is also possible to generate an electromagnetic pulse by way of optical or electric gating using a negative resistance element or a semiconductor element such as a quantum cascade laser, a resonant tunneling diode or a Gunn diode. Furthermore, it is possible to use an oscillator formed by utilizing a nonlinear optical crystal or by using an electronic tube such as a BWO (backward wave oscillator).

A light pulse of difference frequency of two lasers of different types having different laser wavelengths may be used for optical gating instead of the light pulse used in the embodiment and the examples that are described hereinafter. A detection element that may be a semiconductor element such as a Schottky barrier diode or a heat detector such as a bolometer may be used for optical or electric sampling instead of a sampling method of using the Pockels effect, which is an electro-optic effect, or a method of using a photoconductive switch element. Additionally, the present invention is not limited to a method of selecting the timing of gating by branching a single beam of pulse light to generate pump light and probe light so long as the timing of gating at the generating side and the timing of gating at the detecting side are made to substantially agree with each other.

The propagation section for propagating a terahertz pulse may be a transmission line such as a transmission path using a strip line instead of a space section used in the embodiment and the examples that are described hereinafter. In the case of the transmission line, the object of examination can be placed of the transmission line and the dispersing section can be placed in the middle of the transmission line.

Alternatively, in the embodiment and the examples that are described hereinafter, the delaying section is placed in the optical path of probe light, but may be in the optical path of pump light. Since it is sufficient to give rise to a relative delay between the probe light and pump light, a delaying section may be arranged at least on either of the optical paths to relatively shift the delay time. Any means for relatively shifting the timing of optical or electric gating may be used for the purpose of the present invention. Then, as a result, the timing of detection of detecting the electric field intensity can be adjusted. Any arrangement that provides the dispersing section having the frequency-chirping function with group velocity dispersion characteristics may be used for the purpose of the present invention.

(Measuring Apparatus)

Now, an embodiment of the present invention will be described by referring to the drawings.

Figure 2A:
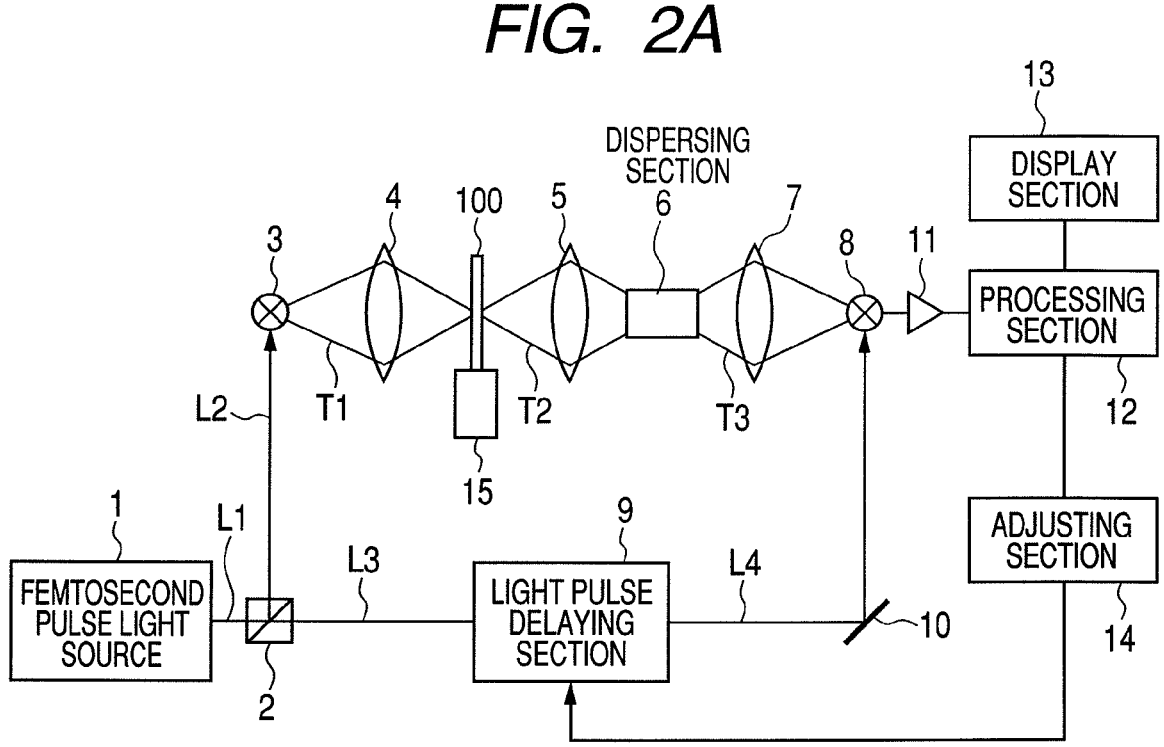
FIG. 2A is a schematic illustration of the terahertz pulse measuring apparatus and the terahertz pulse measuring method of the embodiment of FIGS. 1A through 1C that are used for Example 1, showing the configuration thereof.
Figure 2B:
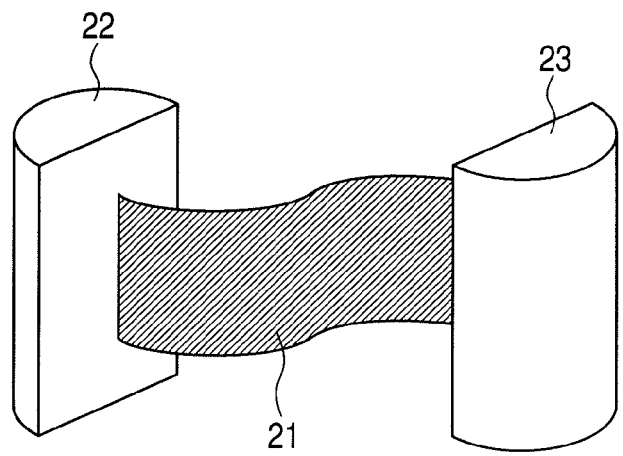
FIG. 2B is a schematic perspective view of the dispersing section of the measuring apparatus of FIGS. 1A through 1C.

FIG. 2A is a schematic illustration of the terahertz pulse measuring apparatus and the terahertz pulse measuring method according to the embodiment of the present invention. FIG. 2B is a schematic perspective view of the dispersing section 6 of the measuring apparatus of FIG. 2A.

In the terahertz pulse measuring apparatus of this embodiment, the femtosecond light pulse L1 emitted from femtosecond pulse light source 1, which may typically be a laser device, is split to produce two light pulses L2 and L3 by a beam splitter 2. The light pulse L2 produced as a result of splitting the light pulse by the beam splitter 2 is used as pump light for generating a terahertz pulse T1 from a terahertz pulse generator 3. The other light pulse, or the light pulse L3, produced as a result of splitting the light pulse by the beam splitter 2 is provided with an optical delay by a light pulse delaying section 9, which is formed typically by using a combination of several planar reflectors and a moving mirror. The light pulse L4 provided with an optical delay becomes probe light for exciting a terahertz pulse detector 8 and detecting a terahertz pulse by way of a mirror 10.

The terahertz pulse T1 generated from the terahertz pulse generator 3 is focused by a focusing optical system 5. An object of examination 100 is arranged at the focus position. The terahertz pulse T2 transmitted through the object of examination 100 is coupled to a dispersing section 6 by the focusing optical system 5 and frequency-chirped by the group velocity dispersion characteristics (the relationship of frequency and group velocity) of the dispersing section 6. The expression of being frequency-chirped refers to a state where the terahertz pulse is subjected to a delay, which depends on the frequency, by the group velocity dispersion characteristics of the dispersing section 6 and temporally stretched.

The terahertz pulse T3 that is frequency-chirped by the dispersing section 6 is focused by the focusing optical system 7 and gets to terahertz pulse detector 8 at time point that varies as a function of frequency. The terahertz pulse detector 8 generates an electric current signal that is proportional to the electric field intensity of the terahertz pulse T3 at the time of incidence of probe light L4. The signal is amplified by an amplifier 11 and subsequently taken into a processing section 12 that is typically formed by using a signal processing circuit and a personal computer. Thus, it is possible to acquire information on the frequency component that corresponds to the time of incidence by appropriately selecting the timing of detection. The timing of detection can be adjusted by the adjusting section 14 that controls the light pulse delaying section 9 according to the signal from the processing section 12.

As described above, with this embodiment, it is possible to acquire electric field information of a specific frequency component without measuring the entire time waveform so that both the spatial change and the temporal change of a specific frequency component can be observed in a relatively short period of time.

A two-dimensional image of the object of examination 100 can be obtained for a specific frequency component by scanning the object of examination 100 at two or more than two points of measurement thereof in a plane perpendicular to the optical axis by means of a scanning stage 15 that is a moving section. It is also possible to obtain a multi-dimensional image of the object of examination 100 for a specific frequency component by multi-dimensionally scanning the object of examination 100 by means of the moving section. With a conventional technique of using THz-TDS, the time waveform of a terahertz pulse needs to be measured on a pixel by pixel basis. Such a measuring operation is time consuming.

Any time can be selected for the timing of detection except the time when the amplitude of the frequency-chirped terahertz pulse T3 is equal to nil, although a result of measurement showing a high SN ratio can be expected when an extremum near a time point that corresponds to the frequency to be observed is selected for the timing of detection. For such an arrangement, the adjusting section 14 is provided with extremum-finding means for finding an extremum of electric field intensity at or near the timing of detection. The phase characteristic of the terahertz pulse T3 can fluctuate due to fluctuations of the thickness of the object of examination 100 and/or changes in the external humidity and such fluctuations by turn can give rise to noise. Since the extremum-finding means constantly search for an extremum for the measurement, it is an effective means from the viewpoint of compensating the influence of fluctuations of the phase characteristic.
(Adjustment of Timing of Detection by Means of Group Delay Characteristic)

Figure 3:
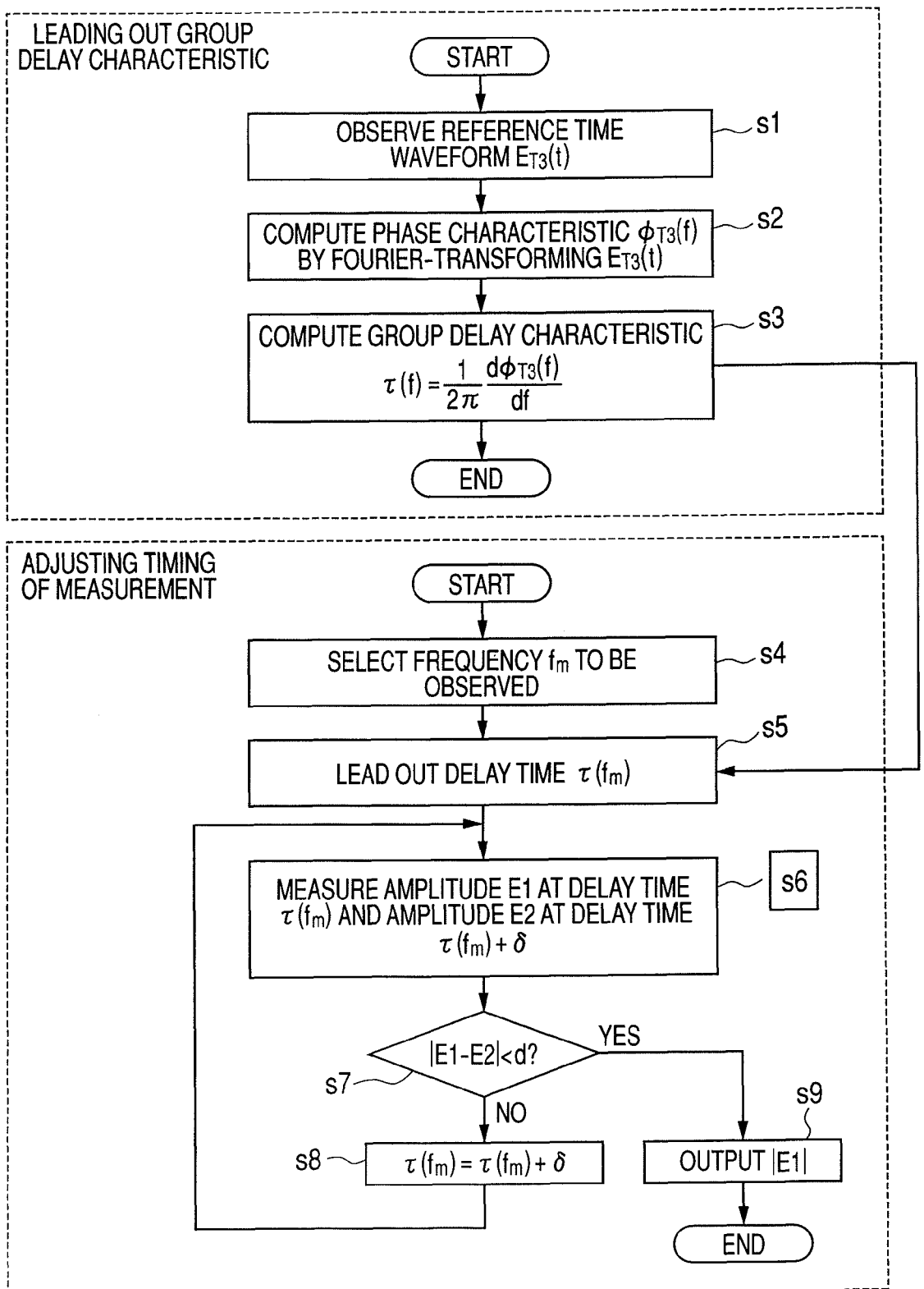
FIG. 3 is a flowchart of the operation of the adjusting section having an extremum-finding section.

FIG. 3 is a flowchart of the operation of the adjusting section 14 having extremum-finding means in a measuring process. The operation of adjusting the timing of detection includes a step of leading out the group delay characteristic $\tau(f)$ (the relationship of each frequency component and delay time) of the terahertz pulse T3 and a step of adjusting the timing of detection by referring to the group delay characteristic $\tau(f)$. The adjusting operation is controlled by the processing section 12.

When leading out the group delay characteristic $\tau(f)$, firstly the time waveform $E_{T3}(t)$ of the frequency-chirped terahertz pulse T3 is observed (Step s1). While the terahertz pulse T3 is observed in a state where the object of examination is placed in position, it may alternatively be observed in a state where the object of examination is not placed when the delay due to the object of examination is negligible.

Then, the phase characteristic $\phi_{T3}(f)$ of the terahertz pulse T3 is determined by Fourier-transforming $E_{T3}(t)$ (Step s2). Then, the group delay characteristic $\tau(f)$ is determined by means of the formula shown below, using the determined phase characteristic $\phi_{T3}(f)$ (Step s3).

$$\tau(f) = \frac{1}{2\pi} \frac{d\phi_{T3}(f)}{df}$$

On the other hand, in the step of adjusting the timing of detection, firstly the frequency $f_m$ to be observed is selected (Step s4) and the time point $\tau(f_m)$ that corresponds to the frequency $f_m$ to be observed is lead out from the group delay characteristic $\tau(f)$ determined in Step s3 (Step s5). Then, the amplitudes E1 and E2 of the terahertz pulse T3 are measured respectively at time point $\tau(f_m)$ and at time point $\tau(f_m)+\delta$ (Step s6). A constant d that is sufficiently smaller than the cycle period of the terahertz pulse T3 near the time point $\tau(f_m)$ is selected. Then, the difference of E1 and E2, or |E1−E2|, and the constant d is compared (Step s7) and |E1| is output when |E1−E2|<d (Step s9), whereas $\tau(f_m)=\tau(f_m)+\delta$ is made to hold true when |E1−E2|≧d (Step s8) and E1 and E2 are measured once again and the measurement is repeated until |E1−E2|<d is obtained. The constant d is desirably substantially equal to the noise level.

Thus, an extremum at or near time point $\tau(f_m)$ that correspond to the frequency $f_m$ to be observed can be output by selecting appropriate values respectively for the constants $\delta$ and d.

The present invention is by no means limited to the arrangement of the adjusting section described above in detail. For example, the group delay characteristic $\tau(f)$ can be determined by measuring the cycle period of the observed time waveform at or near the delay time $\tau$ and using the reciprocal of the cycle period. Alternatively, the group delay characteristic $\tau(f)$ can be determined from the structure of the dispersing section 6 by means of an analytical technique.

When the object of examination is unknown and it is difficult to predict the group delay characteristic $\tau(f)$, it is desirable to lead out the group delay characteristic $\tau(f)$, following the flowchart of FIG. 3, before the actual measurement operation. When, on the other hand, the object of examination is known as in the case of examination of a medicine, the measurement can be conducted quickly by storing the group delay characteristic $\tau(f)$ in a database in advance.
(Characteristic of Dispersing Section)

The characteristic of the dispersing section 6 is defined by the group delay characteristic $\tau(f)$ and the transmission factor T. In order to uniquely determine the timing of incidence of probe light corresponding to each frequency component, it is desirable to make the group delay dispersion $d\tau(f)/df$ show a same sign in the frequency region to be observed.

In the measuring operation using the extremum-finding means, the frequency resolving power can be made small when the group delay dispersion $d\tau(f)/df$ is large (to achieve a high resolving power). To obtain a frequency resolving power not larger than Δf at and near the frequency component f, the dispersing section 6 needs to satisfy the requirement of the following formula.

$$d\tau(f)/df \gtrsim 1/f \cdot \Delta f$$

From the restriction of the uncertainty principle, a frequency characteristic having a narrow band (and hence sharp) can be observed when the group delay dispersion dτ(f)/df is large. If the frequency characteristic is of the Gaussian type, the dispersing section needs to satisfy the requirement of the following formula in order to observe the frequency characteristic for not more than the frequency band Δv.

$$d\tau(f)/df \gtrsim 0.441/\Delta v^2$$

The electric field intensity of a frequency-chirped terahertz pulse becomes low when the group delay dispersion dτ(f)/df is large because the pulse energy is dispersed on the time axis. To obtain an electric field intensity value not lower than the noise level N, the dispersing section needs to satisfy the requirement of the following formula.

$$\int_{-\infty}^{\infty} E_{T2} T \exp(-j\phi) \exp(j2\pi ft) df \gtrsim N$$

In the above formula, $E_{T2}$ is the Fourier transform of the terahertz pulse T2 before it is frequency-chirped by the dispersing section 6, which is a complex number. The phase characteristic φ is expressed by the following formula, using the group delay characteristic τ(f).

$$\phi(f) = 2\pi \int_0^f \tau(f) \cdot df$$

(Configuration of Dispersing Section)

The dispersing section 6 that satisfies the above requirement can be realized by means of a waveguide structure 21 as shown in FIG. 2B. The waveguide is preferably a single mode waveguide in the frequency region to be observed in order to suppress the influence of inter-mode interference. Additionally, it is a propagation mode waveguide other than the TEM mode (the mode of waveguide where the component of electric field and that of magnetic field are equal to nil in the direction of propagation of wave) in order to effectively obtain a large group velocity dispersion. A dielectric slab structure, a dielectric fiber structure or a hollow waveguide structure may preferably be used as the waveguide. The coupling loss can be minimized by arranging a launching coupling system 22 and an emitting coupling system 23 that are suited for the light incident end and the light emitting end of the waveguide.

(Following and Detecting Terahertz Pulse on Real Time Basis)

Figure 4:
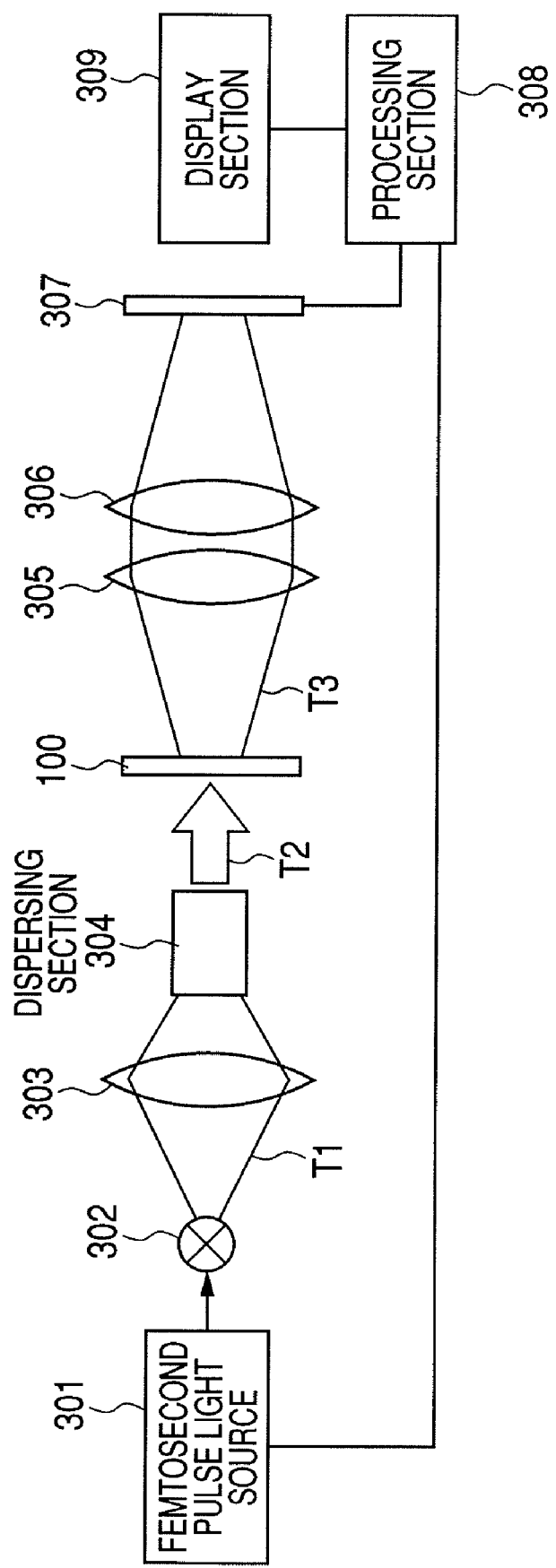
FIG. 4 is a schematic illustration of an imaging apparatus using an array detector.

The time dependency of the intensity of a terahertz pulse can be directly detected by means of a detector such as a Shottky barrier diode without sampling, using probe light, by further stretching the terahertz pulse and making it show a pulse width that can be followed by a relatively high speed detector such as a Shottky barrier diode by means of the dispersing section. When doing so, the spectral characteristic can be obtained at high speed by converting the time axis of the acquired waveform into the frequency axis by means of the group delay characteristic. FIG. 4 is a schematic illustration of an imaging apparatus using an array detector. The terahertz pulse T1 generated from the terahertz generator 302 focused by a lens 303 and then stretched by a dispersing section 304 before being irradiated onto an object of examination 100. The pulse width of the stretched terahertz pulse T2 may be 1 microsecond for instance. The terahertz pulse T3 that is transmitted through the object of examination 100 is imaged on the array detector 307 formed by using a Schottky barrier diode array by means of an imaging optical system having lenses 305 and 306. Each pixel of the array detector detects the time waveform of the terahertz pulse by detecting the terahertz pulse in synchronism with the repetitive frequency of femtosecond pulse light source 301. The waveform information obtained by the measurement is converted into spectral information by a processing section 308 and displayed on a display section 309 as an image corresponding to a desired frequency component.

When the peak output of the terahertz pulse generated from the generator is very large or when the dispersing section is formed by a medium having a very large nonlinear coefficient, the nonlinear effect of the dispersing section can be effectively utilized. For example, when the nonlinear effect of the dispersing section 304 is unnegligible in FIG. 4, the terahertz pulse T1 that enters the dispersing section 304 is subjected to frequency modulation due to the nonlinear effect (SPM: self phase modulation) in the dispersing section 304. In other words, the terahertz pulse T2 that passes through the dispersing section 304 can show a broader band than the terahertz pulse T1 that enters the dispersing section 304. The dispersing section 304 has a normal dispersion characteristic to stretch the pulse. Such an effect can be obtained when the dispersing section 304 is arranged upstream relative to the object of examination 100.

Now, the present invention will be described by way of Examples.

Example 1

Example 1 will be described below by referring to FIG. 2A. This example corresponds to the above-described embodiment. Referring to FIG. 2A, the femtosecond light pulse L1 having a central wavelength of 800 nm and a pulse width of 50 fs that is emitted from a titanium-sapphire laser 1 is split to produce light pulse L2 and light pulse L3 by a beam splitter 2.

The light pulse L2 produced from the beam splitter 3 as a result of splitting the light pulse L1 becomes pump light for generating a terahertz pulse T1. An optical delay is given to the other light pulse, or the light pulse L3, produced from the beam splitter 2 as a result of splitting the light pulse L1 by a light pulse delaying section 9 that is formed by combining several planar reflectors. The light pulse L4 produced as a result of the optical delay becomes probe light for exciting terahertz pulse detector 8 to detect the terahertz pulse T3. Both the average intensity of pump light and that of probe light are adjusted by respective optical attenuators (not shown) on their light paths so as to be equal to 5 mW.

In this example, photoconductive switches, each of which is prepared by forming a dipole antenna showing a gap interval of 5 μm on an LT-GaAs film grown on a GaAs substrate by low temperature growth, are respectively employed for the terahertz pulse generator 3 and the detector 8. At the generator side, a terahertz pulse T1 is generated by applying a voltage of 10V to the gap of the dipole antenna and allowing pump light L2 to enter the gap. The terahertz pulse T1 generated from the terahertz pulse generator 3 is focused by a focusing optical system 4. An object of examination 100 is arranged at the focus position. The terahertz pulse T2 transmitted through the object of examination 100 is coupled to a dispersing section 6 by the focusing optical system 5 and frequency-chirped. In this example, elements that do not give rise to any multiple-reflection such as paraboloidal mirror are appropriately employed for each focusing optical system in order to prevent unnecessary interference from appearing to the frequency-chirped terahertz pulse.

At the detector side, on the other hand, when probe light L4 enters the gap of the dipole antenna, the electric current that is proportional to the electric field of the terahertz pulse T3 is amplified by amplifier 11 and subsequently taken into processing section 12. A dynamic range of three digits or more can be obtained relatively easily by modulating the terahertz wave at 1 KHz at the time of generation and detecting the signal by lock-in detection.

Figure 5A:
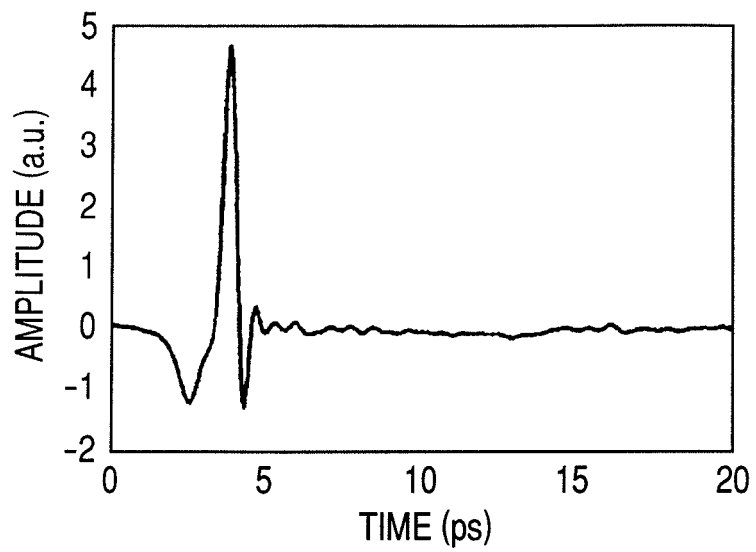
FIG. 5A is a graph of the time waveform of a terahertz pulse observed by removing the object of examination and the dispersing section from the measuring apparatus of FIGS. 1A through 1C.

FIG. 5A is a graph of the time waveform of an exemplar terahertz pulse measured by removing the object of examination 100 and the dispersing section 6 from the measuring apparatus of FIG. 2A and sequentially changing the optical delay by the light pulse delaying section 9. The measurement is conducted in a condition where the optical path of the terahertz pulse is replaced by nitrogen in order to suppress the influence of steam. The measurement of the terahertz pulse takes about 6 minutes with temporal resolving power of 20 fs as the terahertz pulse is measured at 4,000 points.

Now, the example will be described in terms of an object of examination 100 and a dispersing section 6 that are specifically provided. A high density polyethylene type slab waveguide is employed for the dispersing section 6. A characteristic that makes the waveguide operates in a single mode of $TM_0$ mode in a frequency range not higher than about 4 THz and the group delay dispersion $d\tau(f)/df$ constantly positive can be obtained for the waveguide by selecting a thickness of 40 μm for the waveguide. Additionally, a waveguide length of 100 mm is selected by considering the frequency resolving power and the frequency band. For the purpose of simplicity, the material absorption of polyethylene and the coupling loss of the terahertz pulse and the waveguide are neglected here.

Figure 5B:
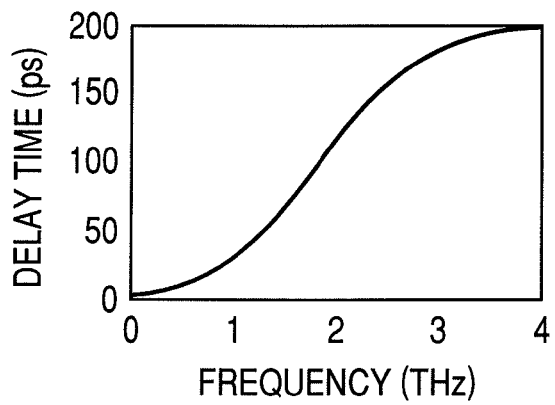
FIG. 5B is a graph showing the results of numerical calculations for a group delay characteristic performed by the measuring apparatus of FIGS. 1A through 1C when a high density polyethylene slab waveguide is used for the dispersing section.

The group delay characteristic as shown in FIG. 5B can be determined from the phase characteristic of the waveguide that is obtained by numerical calculations and the time waveform of FIG. 5A. From FIG. 5B, it will be seen that the frequency component of 0 to 4 THz uniquely corresponds to a delay time of 0 to 200 ps. It will also be seen that the group delay dispersion $d\tau(f)/df$ is constantly positive.

Figure 5C:
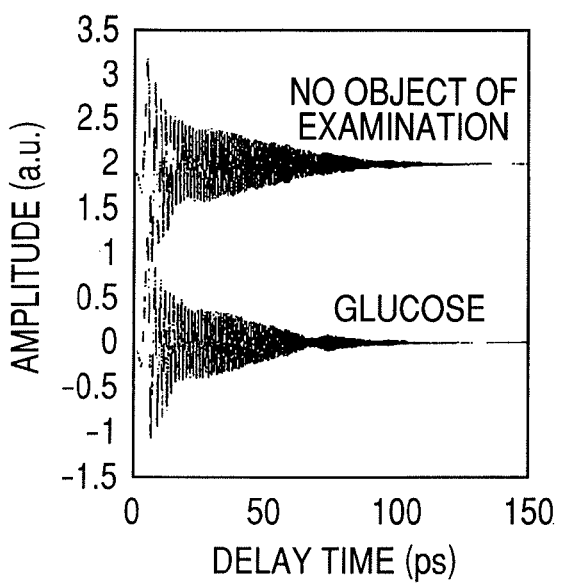
FIG. 5C is a graph showing the results of numerical calculations for a terahertz pulse time waveform that is frequency-chirped by the measuring apparatus of FIGS. 1A through 1C.

FIG. 5C is a graph showing the results of numerical calculations for a terahertz pulse that is frequency-chirped by the dispersing section 6 when there is no object of examination and when compacted glucose is placed as object of examination.

Figure 6:
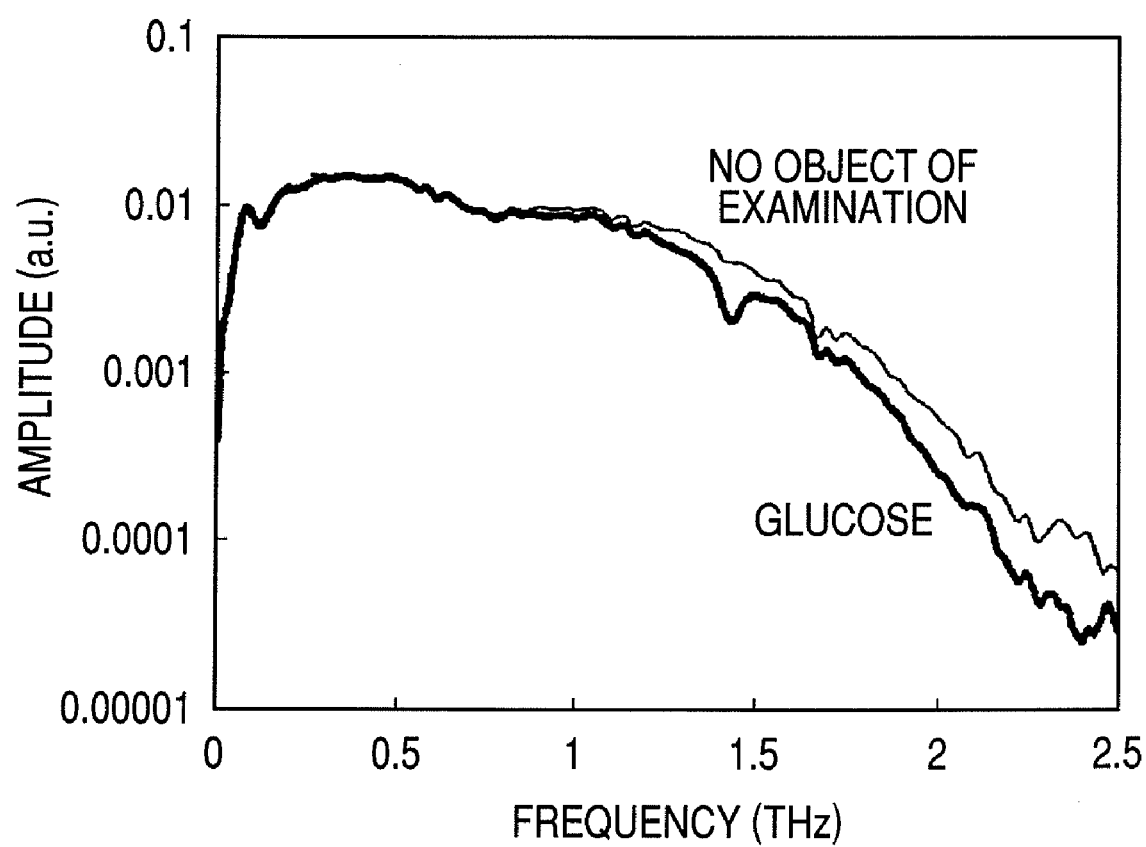
FIG. 6 is a graph showing the spectral characteristics obtained by Fourier-transforming each of the terahertz pulse time waveforms of FIG. 5C.

When compared with the instance where there is no object of examination, in the case where glucose is placed as object of examination, a recessed type envelope waveform is observed and the recess is centered at a delay time of 66 ps. From FIG. 5B, it will be seen that the delay time of 66 ps corresponds to a frequency of 1.45 THz. FIG. 6 is a graph showing the frequency characteristics obtained by Fourier-transforming each of the time waveforms of FIG. 5C. A fingerprint spectrum showing a peak frequency at about 1.45 THz that is produced by absorption of glucose is observable. This frequency agrees with the frequency estimated from the delay time. Additionally, the ratio $E_g/E_0$ of the amplitude $E_g$ observed when glucose is placed as object of examination to the amplitude $E_0$ observed when there is no object of examination at the frequency of 1.45 THz is 0.41 for the time waveform of FIG. 5C and 0.45 for the frequency spectrum of FIG. 6 to evidence a substantial agreement.

Thus, when a high density polyethylene type slab waveguide is used for the dispersing section 6 of the terahertz pulse measuring apparatus of FIG. 2A, the change in the absorption characteristic at the frequency of 1.45 THz attributable to molecular oscillation of glucose can be measured by adjusting the timing of incidence of probe light to an extremum near the delay time of 66 ps.

While a polyethylene type slab waveguide is used for forming the dispersing section 6 in this example, the present invention is by no means limited thereto. For example, the group velocity dispersion of a material showing little absorption relative to terahertz waves selected from polymers such as Teflon®, semiconductor materials such as high resistance silicon, inorganic materials such as quartz and so on may alternatively be utilized for the purpose of the present invention. Still alternatively, any structure such as waveguide structure, a multilayer film structure or a photonic crystal may be utilized for the purpose of the invention.

As seen from this example, amplitude information for the frequency to be observed can be obtained without acquiring the time waveform of a frequency-chirped terahertz pulse by detecting the terahertz pulse at a timing of detection that corresponds to the frequency to be measured. Therefore, information on physical properties of an object of examination can be obtained relatively at high speed. Additionally, a frequency to be observed can be flexibly selected within a relatively broad frequency range by means of an adjusting section.

Example 2

Imaging Apparatus

Figure 7:
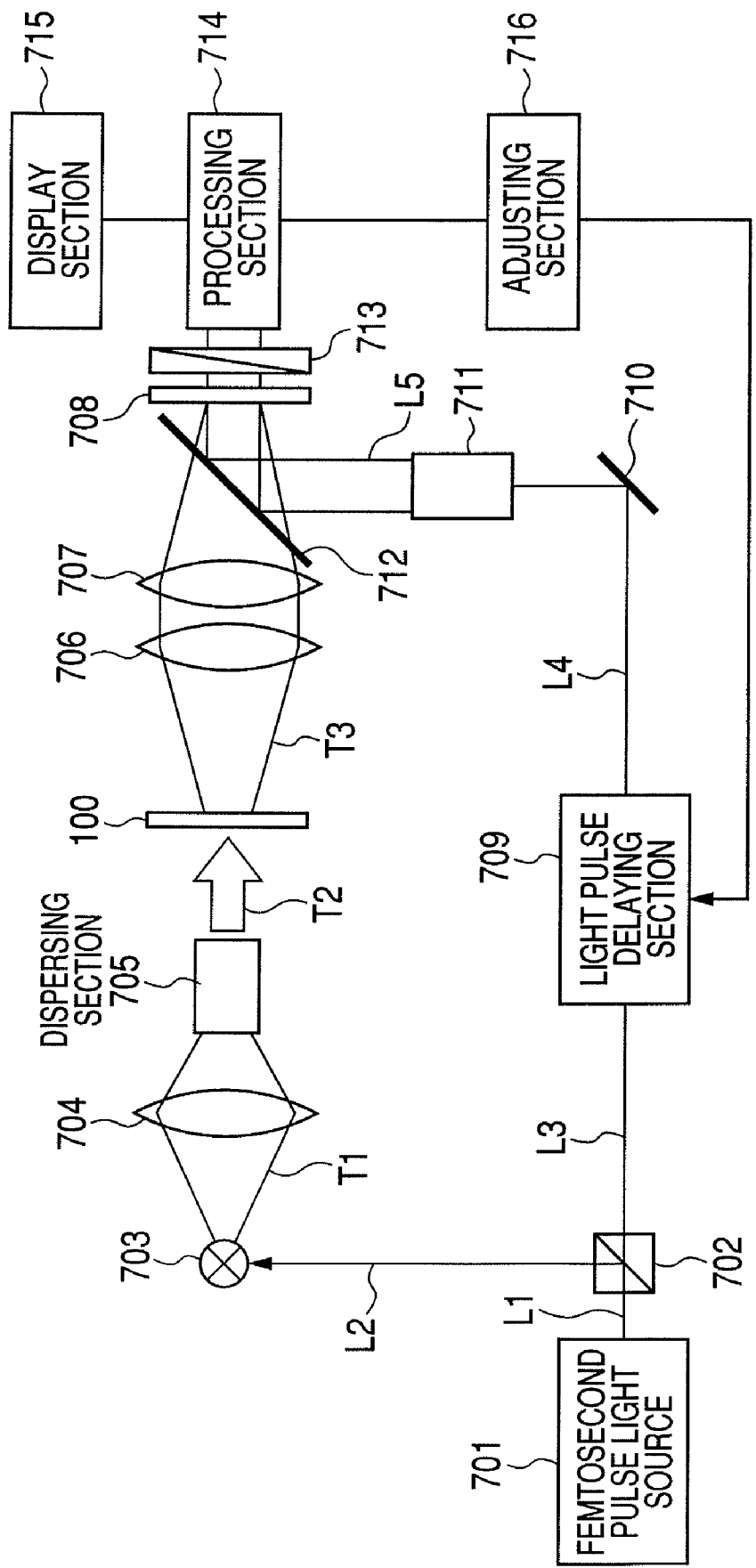
FIG. 7 is a schematic illustration of the terahertz pulse measuring apparatus and the terahertz pulse measuring method used for Example 2, showing the configuration thereof.

Now, Example 2 will be described below by referring to FIG. 7. While the apparatus of Example 2 of this invention operates substantially same as the apparatus of Example 1, the apparatus of FIG. 2 differs from the apparatus of Example 1 in that a two-dimensional image of an object of examination 100 that is irradiated with a terahertz wave is collectively obtained by shooting the object of examination 100 by means of an electro-optic crystal 708 and a CCD camera 714.

In this example, the femtosecond light pulse L1 emitted from a femtosecond pulse light source 701 of a linearly polarized femtosecond pulse light that is a titanium-sapphire laser is split to produce light pulse L2 and light pulse L3 by a beam splitter 702. The light pulse L2 produced as a result of splitting the light pulse by the beam splitter 702 is used as pump light for exciting a terahertz pulse generator 703 that is formed by using a photoconductive antenna. The terahertz pulse T1 generated from the terahertz pulse generator 703 is made to pass through a focusing optical system 704 and then frequency-chirped by a dispersing section 705 that is formed by using a high density polyethylene slab waveguide.

The terahertz pulse T2 that is frequency-chirped by the dispersing section 705 is made to collectively irradiate the two-dimensional region of the object of examination 100. After passing through the object of examination 100, the terahertz pulse T3 is transmitted through a beam splitter 712 after passing through lenses 706 and 707 that form an imaging optical system and subsequently collectively received by an electro-optic crystal 708 such as ZnTe. A two-dimensional image of the object of examination 100 is formed on a two-dimensional region of the electro-optic crystal 708 that corresponds to it by placing the electro-optic crystal 708 at the image forming position of the object of examination 100.

On the other hand, the other light pulse, or the light pulse L3, produced as a result of splitting the light pulse by the beam splitter 702 is provided with an optical delay by a light pulse delaying section 709. Subsequently, the beam diameter of the optically delayed light pulse L4 is expanded by a beam expander 711 after being reflected by a mirror 710 and becomes probe light L5 for detecting the terahertz pulse T3.

The beam expander 711 forms a probe light irradiation section for collectively irradiating probe light to a two-dimensional region of the electro-optic crystal 708 that corresponds to the two-dimensional region of the object of examination 100. In this way, probe light L5 that is linearly polarized light is reflected by the beam splitter 712 and subsequently transmitted through the above-described two-dimensional region of the electro-optic crystal 708. The state of polarization of probe light L5 is modulated at the electro-optic crystal 708 according to the electric field intensity of the terahertz pulse T3 at the time when probe light L5 strikes the electro-optic crystal 708. A specific polarized component of probe light L5, whose state of polarization is modulated at the electro-optic crystal 708, is extracted by an optical analyzer 713 that operates as an analyzer section and the light intensity distribution of probe light L5 is collectively detected by a two-dimensional CCD camera 714.

In this example, a dispersing section similar to that of Example 1 can be used when the dispersing section 705 is arranged at a position between the terahertz pulse generator 703 and the object of examination 100. Alternatively, the dispersing section 705 may be arranged between the object of examination 100 and the electro-optic crystal 708. If, such is the case, however, the dispersing section 705 needs to be formed by using a fiber bundle so as to be able to hold a two-dimensional image. The influence of the phase change in the two-dimensional region of the object of examination 100 that arises due to collective irradiation of the two-dimensional region can be reduced by optimally designing the optical path length of each fiber element of the fiber bundle.

Figure 8:
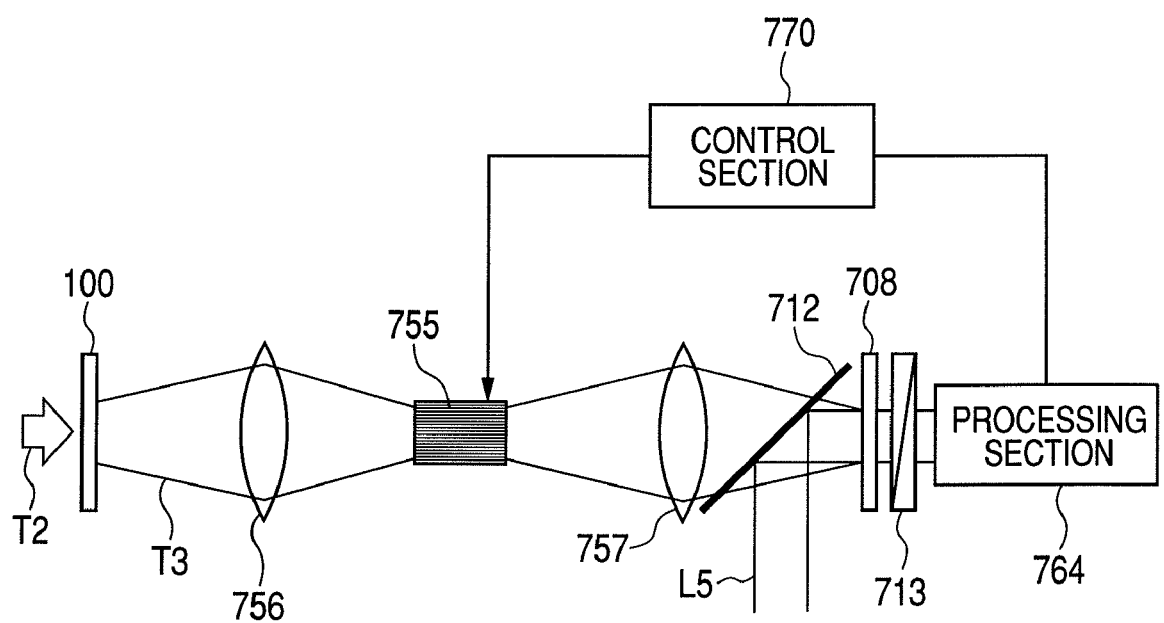
FIG. 8 is a schematic illustration of the terahertz pulse measuring apparatus and the terahertz pulse measuring method used for a modified example of Example 2, showing the configuration thereof.

Now, reduction of noise by feedback control of a modified example where a dispersing section of a fiber bundle having such a bundle structure is used will be described below by referring to FIG. 8. FIG. 8 schematically illustrates the arrangement of the optical path from the object of examination 100 to the electro-optic crystal 708. The terahertz pulse T3 transmitted through the object of examination 100 forms an image thereof at the light receiving end of the dispersing section (fiber bundle) 755 by way of an imaging optical system 756 such as a lens. The terahertz pulse that is frequency-chirped by the dispersing section 755 forms an image thereof on the electro-optic crystal 708 after being transmitted through the beam splitter 712. Probe light L5 that is linearly polarized light is already described above.

For the above-described arrangement, the dispersing section 755 is formed by a fiber bundle and an optical path control means for controlling the optical path in each fiber by applying heat or pressure to at least a part thereof. Control section 770 analyzes the amplitude intensity at the time of measurement of the terahertz pulse emitted from each fiber by means of the two-dimensional image observed by a processing section (two-dimensional CCD camera) 764 and controls the optical path control means so as to make the absolute value of the amplitude intensity show a maximum value close to the time of measurement. With this technique, the terahertz pulse always takes a maximum value in the plane being observed so that the noise caused by a phase change in the plane of the object of examination 100 can be reduced to a large extent.

As described above, in Example 2, the timing of incidence of probe light L5 can be appropriately selected by the adjusting section 716 for adjusting the light pulse delaying section 709 according to the control signal from the processing section 714 or the processing section 764 and a two-dimensional image of the frequency component that correspond to the timing of incidence can be collectively observed. Then, the two-dimensional image can be displayed on the display section 715. Therefore, the arrangement of this example is effective for real time imaging that requires monochromaticity.

Example 3

Dispersing Section of Hollow Waveguide

Figure 9:
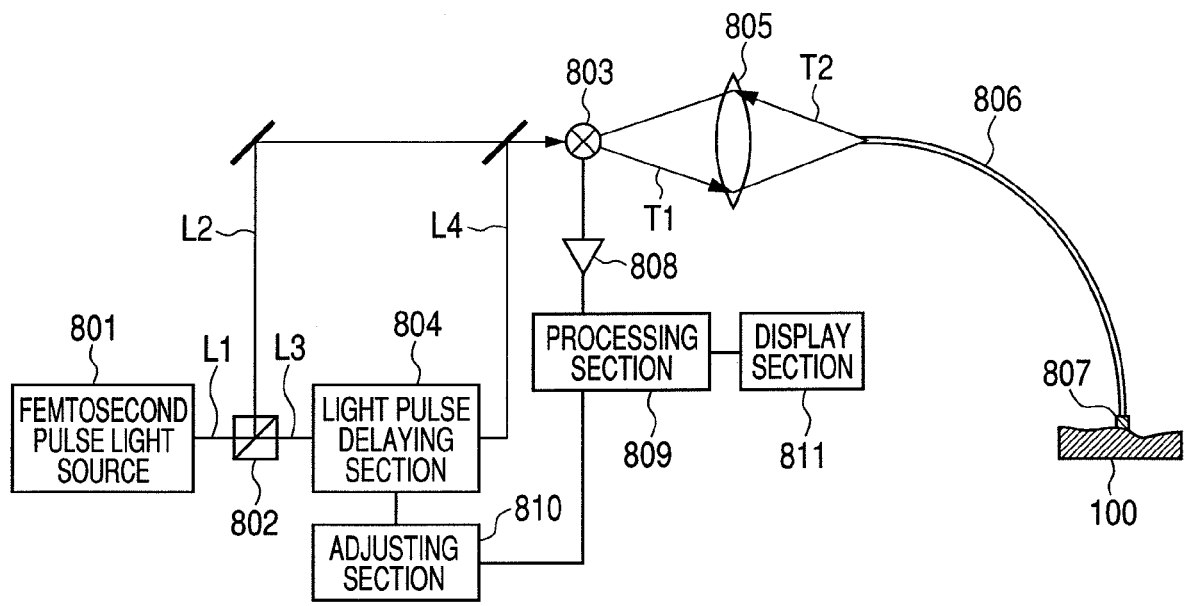
FIG. 9 is a schematic illustration of the terahertz pulse measuring apparatus and the terahertz pulse measuring method used for Example 3, showing the configuration thereof.
Figure 10:
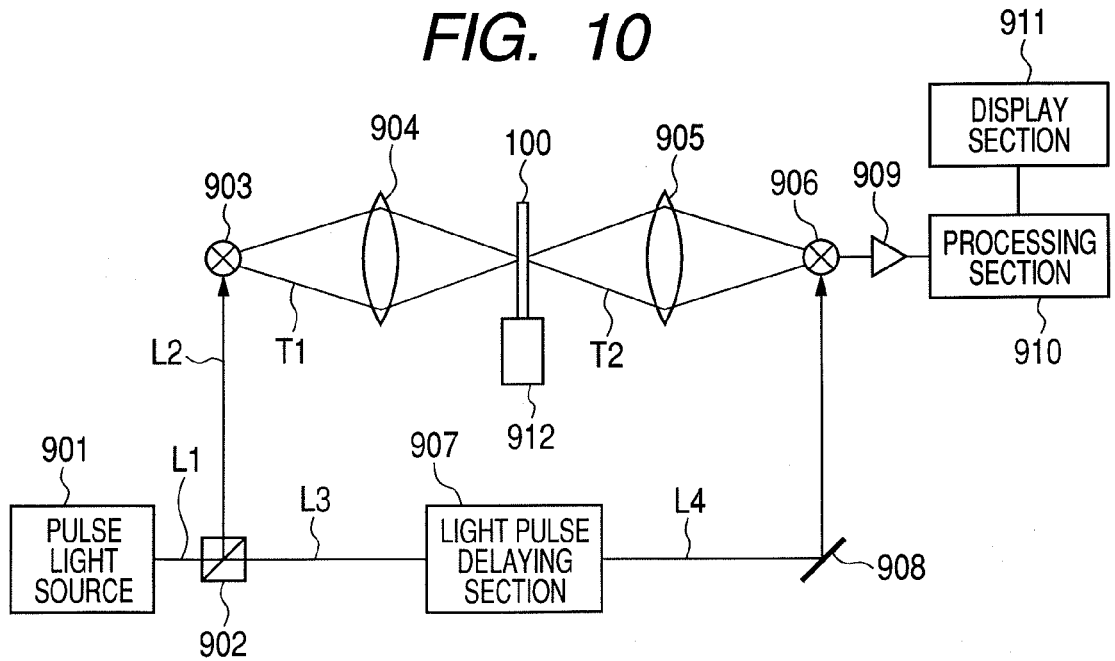
FIG. 10 is a schematic illustration of a known terahertz pulse measuring apparatus, showing the configuration thereof.

FIG. 9 is a schematic illustration of the terahertz pulse measuring apparatus of Example 3 that is arranged to navigate a terahertz pulse up to an affected part of a patient by using a terahertz wave for the purpose of an endoscope operation or a dental treatment. While the terahertz pulse measuring apparatus of Example 3 operates substantially same as that of Example 1, the apparatus of Example 3 differs from the latter apparatus in that a single photoconductive antenna 803 is used to form a terahertz pulse generator and a detector and a dispersing section 806 is made to take the role of guiding a terahertz pulse to the affected part (object of examination) 100.

In Example 3, a short pulse fiber laser with a wavelength of 1.56 μm, a pulse width of 50 fs, a repetitive frequency of 48 MHz and an average output power of 100 mW is employed as a femtosecond pulse light source 801. The fiber laser is relatively small and highly stable so that it can suitably be used for medical applications like this example. The femtosecond light pulse L1 emitted from the femtosecond pulse light source 801 is split to produce light pulse L2 and light pulse L3 by a beam splitter 802.

Pump light L2 produced as a result of splitting the light pulse L1 by the beam splitter 802 excites a terahertz transceiver 803 formed by using a photoconductive antenna to which a voltage is being applied to generate a terahertz pulse T1. The photoconductive antenna employed here can be prepared in a manner as described below. An Au dipole antenna is formed on an $In_{0.53}Ga_{0.47}As$ thin film produced by ion beam epitaxial growth on an InP substrate at a substrate temperature of 180° C. with a gap of 5 μm. Then, the $In_{0.53}Ga_{0.47}As$ thin film on which the dipole antenna formed is separated from the InP substrate by polishing and etching the substrate is transferred onto a high resistance silicon substrate showing a resistivity of 10 kW·cm. The resistivity of the $In_{0.53}Ga_{0.47}As$ thin film is preferably improved by injecting Fe and Br and/or adding Be in the growth step.

The terahertz pulse T1 generated from the terahertz transceiver 803 is coupled to the dispersing section 806 6y way of a launching coupler 805. Since the dispersing section 806 is made to have a function of guiding a terahertz pulse to affected part 100, the dispersing section 806 needs to be a waveguide structure showing a low loss level and a high degree of flexibility. A hollow waveguide formed by a glass capillary tube having an inner diameter not larger than 2 mm whose inner surface is coated with a silver thin film may suitably be used for the dispersing section 806. Since a hollow waveguide showing an inner diameter of 1 mm and a length of 1 m can transmit a terahertz wave with a transmission loss of about 3 dB and operates in a quasi-single mode of $TE_{11}$ mode, the interference effect between the modes can be lowered. Further, the inside of the waveguide can be purged by nitrogen whenever necessary.

The terahertz pulse T2 coupled to the dispersing section 806 is propagated in the dispersing section 806, while it is being frequency-chirped, and irradiated to the object of examination 100 by way of a window member 807 arranged at the front end of the dispersing section. The window member 807 is arranged to prevent body fluid from entering the inside of the hollow waveguide. It is preferably made of a low refractive index material such as quartz or polyethylene. The focusing effect can be dramatically improved by providing the window member 807 with a lens function. The window member 807 is preferably held in contact with the object of examination 100 during the measurement process in order to keep the optical path length of the interface between the terahertz transceiver 803 and the object of examination 100 to a constant level.

Part of the terahertz pulse irradiated onto the object of examination 100 is reflected by the interface of the object of examination and enters the dispersing section 806 by way of the window member 807. Then, it is propagated in the dispersing section 806, while it is being frequency-chirped. Subsequently, it enters the terahertz transceiver 803 by way of the launching coupler 805. Therefore, the terahertz pulse is delayed to an extent that corresponds to twice of the waveguide length of the dispersing section 806.

The other light pulse, or the light pulse L3, that is produced as a result of splitting the light pulse L1 by the beam splitter 802 is same as that of Example 1. Thus, it is provided with an optical delay by a light pulse delaying section 804 to become light pulse L4. The light pulse L4 becomes probe light for exciting the terahertz transceiver 803 and detecting a terahertz pulse.

The terahertz transceiver 803 generates an electric current signal that is proportional to the electric field of the terahertz pulse T2 reflected from the object of examination 100 at the time when probe light L4 that corresponds to the frequency to be observed enters it. This signal is amplified by an amplifier 808 and subsequently taken into a processing section 809. The results obtained by the processing section 809 can be displayed on a display section 811.

The time waveform of the terahertz pulse T2 obtained when a metal mirror such as an aluminum mirror is arranged instead of the object of examination 100 as shown in FIG. 9 may be used as reference signal from which the group delay characteristic is to be led out by the adjusting section 810 that determines the timing of receiving probe light L4.

As described above, frequency-chirping by group velocity dispersion of a waveguide can give rise to a prolonged measurement time so that the use of a low loss transmission medium such as a hollow waveguide is not easy with conventional THz-TDS. However, according to the present invention, it is possible to realize a highly monochromatic real time measurement by observing the time waveform for a reference signal for once.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application Nos. 2008-009896, filed Jan. 18, 2008 and 2008-300302, filed Nov. 26, 2008, which are hereby incorporated by reference herein in their entirety.

The invention claimed is:

1. An apparatus, comprising:
a generating section for generating a terahertz wave;
a dispersing section for dispersing the terahertz wave generated by the generating section so that a time waveform of the terahertz wave has an electric field intensity distribution relative to frequency, by delaying the terahertz wave depending on frequency; and
a detecting section for detecting an electric field intensity of the terahertz wave dispersed by the dispersing section,
wherein the apparatus is so configured as to be capable of acquiring an electric field intensity for each frequency from a relation between time and frequency of the time waveform obtained by using a dispersion characteristic of the dispersing section.

2. The apparatus according to claim 1, further comprising:
a delaying section for varying a timing of generating or detecting the terahertz wave; and
an adjusting section for adjusting the timing so as to obtain the electric field intensity at a predetermined frequency by using the relation between time and frequency of the time waveform.

3. The apparatus according to claim 1, wherein
the detecting section includes a detector that is capable of following the terahertz wave dispersed by the dispersing section on a real time basis, and
the electric field intensity detected by the detecting section is an envelope of the time waveform of the terahertz wave dispersed by the dispersing section.

4. The apparatus according to claim 1, further comprising:
an irradiation section for irradiating an object with a terahertz pulse which is generated by irradiating the generating section with pump light; and
a probe light irradiation section for collectively irradiating a two-dimensional region of an electro-optic crystal with probe light to be used for irradiating the detection section, the probe light irradiation section being so arranged as to collectively irradiating a two-dimensional region of the object with the terahertz pulse, the two-dimensional region of the electro-optic crystal corresponding to the two-dimensional region of the object, in order to detect an electric field intensity of the terahertz pulse transmitted through or reflected by the object, wherein
the detecting section is formed by:
the electro-optic crystal;
an analyzer section for extracting a specific polarized component of the probe light whose polarized state is modulated by the terahertz pulse transmitted through the electro-optic crystal; and
a detector for collectively detecting the probe light extracted by the analyzer section in a two-dimensional region corresponding to the two-dimensional region of the object.

5. The apparatus according to claim 4, wherein the dispersing section is a waveguide structure arranged between the generating section and the object or between the object and the detecting section.

6. The apparatus according to claim 1, wherein
the dispersing section makes a group delay dispersion $d\tau(f)/df$ show the same sign in a frequency region to be observed, where $\tau(f)$ is a group delay characteristic of the dispersing section and f is frequency.

7. A method, comprising steps of:
generating a first terahertz wave;
dispersing the generated first terahertz wave so that a time waveform of the first terahertz has an electric field intensity distribution relative to frequency, by delaying the first terahertz wave depending on frequency;
detecting an electric field intensity of the dispersed first terahertz wave;
altering a timing of generating or detecting the first terahertz wave;
generating a second terahertz wave;
dispersing the generated second terahertz wave so that a time waveform of the second terahertz has an electric field intensity distribution relative to frequency, by delaying the first terahertz wave depending on frequency;

detecting an electric field intensity of the dispersed second terahertz wave; and acquiring an electric field intensity at a predetermined frequency, wherein the timing is altered so as to obtain the electric field intensity at the predetermined frequency by using a relation between time and frequency of a time waveform that is obtained by using the dispersion characteristic.

8. A measuring apparatus for acquiring information on an object, comprising:

a terahertz pulse generator for generating a terahertz pulse;

a terahertz pulse detector for detecting an electric field intensity of the terahertz pulse;

a first optical system for guiding the terahertz pulse from the terahertz pulse generator to the object; and a second optical system for guiding the terahertz pulse from the object to the terahertz pulse detector, wherein the first optical system or the second optical system includes a dispersing section for temporally stretching the terahertz pulse by delaying the terahertz pulse depending on frequency.

* * * * *